July 4, 1939. N. GRILLO Plant Pat. 334
HYBRID TEA ROSE
Filed Aug. 24, 1938
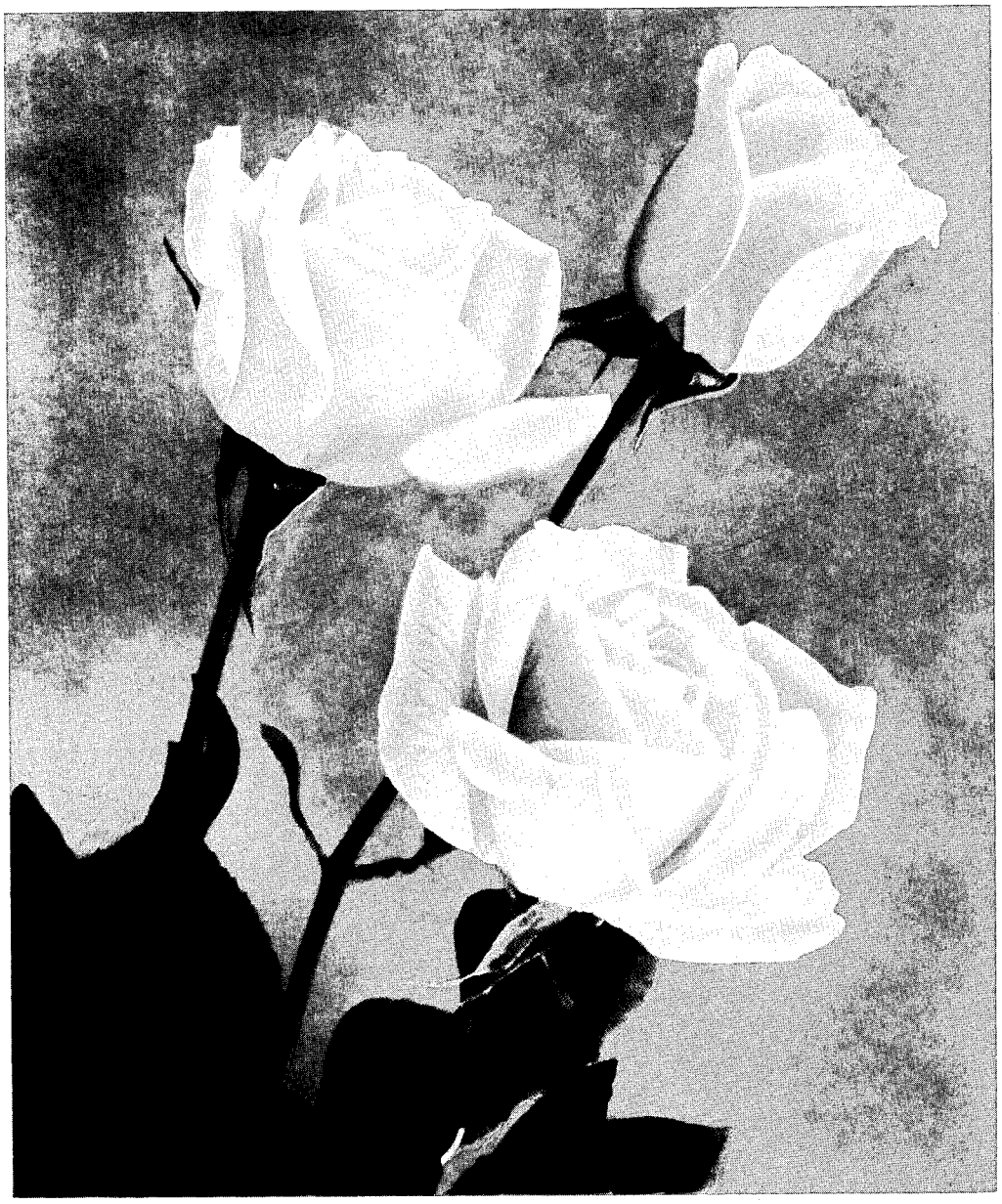
INVENTOR
Nicholas Grillo
By Orville M. Kile
Plant Patent Agent Patented July 4, 1939

Plant Pat. 334

UNITED STATES PATENT OFFICE

334

HYBRID TEA ROSE

Nicholas Grillo, Milldale, Conn.

Application August 24, 1938, Serial No. 226,539

1 Claim. (Cl. 47—61)

My present discovery relates to a new and improved variety of yellow hybrid tea rose plant. It is a sport of Joanna Hill and was discovered by me in my greenhouses in Milldale. It has been asexually reproduced through several generations and its characteristics have persisted.

The original illustration accompanying this application shows buds and flowers of this new variety in various stages of opening and in approximately true form and size. The color in the illustration is that of the warm weather blossoms. In cooler weather the blossoms are darker and the color more evenly distributed.

Following is a detailed description of this new variety of rose plant. Color references are to Ridgway's Color Standards and Nomenclature, except where obviously the ordinary distionary definition is intended.

*The plant*

Foliage:

Abundant.

*Leaves.*—Compound, with 3 to 7 leaflets. Leaflets—oval with sharp apex. Small, the largest terminal leaflets being about 2½ inches in length and about 1½ inches wide. Texture—leathery. Color—between Cress Green and Dark Cress Green (Plate XXXI) on the upper side. The under side approaches Rainette Green (Plate XXXI), although frequently somewhat bronzed.

*Rachis.*—Grooved and usually bronzed above. Under side same shade of green as the leaves, and with several small sharp thorns. Very frail and slender.

*Stipules.*—Clinging. Narrow. Medium in length. Sharp-pointed.

Stems:

Long and very stout. Grass Green (Plate VI). Many thorns present on lower portion of stem, reducing in number proceeding upward.

*Thorns.*—Pink, Downward-pointing. Medium. Hooked.

Growth habits:

Upright bush. Very prolific grower. Continuous bloomer.

*The flower*

Bud:

Medium size. Distinctive shape, being sharp-pointed but relatively short and with large base. When opening, the bud is more "blocky" than the ordinary pointed bud. Before the calyx breaks, the sepals extend far beyond the end of the bud.

Bloom:

*Size.*—Medium, with 4 to 4½ inch spread.

*Form.*—Globular at first. The petals quill and turn backward as the flower ages and the form becomes cactus-like or informal.

*Petalage.*—Double, numbering 35 to 45 in June. Petals: Texture—thick and leathery but soft. Shape—outer petals rounded but inclined to be spatulate. Edges fairly smooth but slightly wavy. Inner petals somewhat curled and irregular. Outer petals curl backward in early stages of maturity. All petals quill and turn backward as flower ages. Color—the color differs somewhat in different seasons. In warm weather the outer petals are Empire Yellow (Plate IV) at the base, and a lighter Straw Yellow (Plate XVI) at the edges. The darker shade extends upward along the veins into the lighter portion of the petal. The inner petals are much darker, ranging from Wax Yellow (Plate XVI) at the base to Empire Yellow (Plate IV) at the tip. The general effect is of a dark yellow center with a surrounding row of lighter yellow petals.

In cooler weather the color is darker and almost uniform throughout. The shade is between Lemon Chrome and Light Cadmium (Plate IV) and is only slightly different from the center of the warm weather blossoms.

A special and important feature of this rose is the constancy of the color of the bloom after cutting, since it does not fade as the flower grows older.

*Reproductive organs*

Stamens:

Many (85 to 90). Uneven lengths. Both anther and filament are Cadmium Yellow (Plate III). They form a ring of dark yellow between the two lighter yellows—one of the petals and the other of the pistils.

Pistils:

Bunched. Greenish-yellow.

Stigmas:

Long, funnel-shaped.

Ovaries:

Partially protruding to form pithy ring between pistils and stamens.

Calyx-tube:

Long and slender.

Sepals:

Simple. Permanent. Medium length. Leave bud as soon as it shows color and turn backward early in the opening process.

*Comparison with Joanna Hill*

This new variety is more like its parent, Joanna Hill, than any other known rose but there are several important differences, as follows:

My new rose is of a distinct shade of yellow both in warm weather and cooler weather and these shades differ from that of Joanna Hill. The color is retained without fading when the flower is fully opened, while the color of Joanna Hill fades as it opens and ages.

My new rose is much more prolific in growth than Joanna Hill.

The form of the bud of my rose differs from that of Joanna Hill, the latter being longer and more slender at the base.

Having thus disclosed my discovery, I claim:

A new and distinct variety of rose plant, substantially as shown and described, characterized particularly by its prolific growth, its flowers of distinctive unfading yellow color differing with the seasons as described, and its buds of distinctive form.

NICHOLAS GRILLO.